United States Patent
Dubois

(10) Patent No.: US 9,630,170 B2
(45) Date of Patent: Apr. 25, 2017

(54) CATALYST PREPARED BY REACTIVE MILLING

(71) Applicant: ARKEMA FRANCE, Colombes (FR)

(72) Inventor: Jean-Luc Dubois, Millery (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/649,099

(22) PCT Filed: Nov. 27, 2013

(86) PCT No.: PCT/FR2013/052872
§ 371 (c)(1),
(2) Date: Jun. 2, 2015

(87) PCT Pub. No.: WO2014/087076
PCT Pub. Date: Jun. 12, 2014

(65) Prior Publication Data
US 2015/0314277 A1 Nov. 5, 2015

(30) Foreign Application Priority Data

Dec. 3, 2012 (FR) .................................. 12 61536

(51) Int. Cl.
| | | |
|---|---|---|
| *B01J 27/32* | (2006.01) | |
| *B01J 38/00* | (2006.01) | |
| *C07C 17/087* | (2006.01) | |
| *C07C 17/07* | (2006.01) | |
| *B01J 37/26* | (2006.01) | |
| *B01J 27/132* | (2006.01) | |
| *B01J 35/02* | (2006.01) | |
| *B01J 37/00* | (2006.01) | |
| *C07C 17/20* | (2006.01) | |
| *B01J 37/04* | (2006.01) | |
| *B01J 27/138* | (2006.01) | |
| *B01J 23/26* | (2006.01) | |
| *B01J 23/34* | (2006.01) | |
| *B01J 23/86* | (2006.01) | |
| *B01J 27/135* | (2006.01) | |

(52) U.S. Cl.
CPC .............. *B01J 27/32* (2013.01); *B01J 27/132* (2013.01); *B01J 27/138* (2013.01); *B01J 35/023* (2013.01); *B01J 37/0036* (2013.01); *B01J 37/04* (2013.01); *B01J 37/26* (2013.01); *B01J 38/00* (2013.01); *C07C 17/07* (2013.01); *C07C 17/087* (2013.01); *C07C 17/206* (2013.01); *B01J 23/26* (2013.01); *B01J 23/34* (2013.01); *B01J 23/86* (2013.01); *B01J 27/135* (2013.01)

(58) Field of Classification Search
None
See application file for complete search history.

(56) References Cited

U.S. PATENT DOCUMENTS

| | | | |
|---|---|---|---|
| 4,169,802 A * | 10/1979 | Basile ................... | C01G 37/02 252/62.51 C |
| 5,523,500 A | 6/1996 | Cheminal et al. | |
| 6,337,299 B1 | 1/2002 | Shibanuma et al. | |
| 6,433,233 B1 | 8/2002 | Kanemura et al. | |
| 8,236,997 B2 * | 8/2012 | Giddis .................. | C07C 17/206 570/168 |
| 2010/0256426 A1 * | 10/2010 | Sakyu ................... | C07C 17/358 570/151 |

FOREIGN PATENT DOCUMENTS

| | | | | |
|---|---|---|---|---|
| CN | 1935360 A | 3/2007 | | |
| CN | 101 385 977 A | 3/2009 | | |
| CN | 102 671 670 A | 9/2012 | | |
| EP | 0 657 408 A1 | 6/1995 | | |
| FR | 2 684 567 A1 | 6/1993 | | |
| FR | EP 0657408 A1 * | 6/1995 | .............. | B01J 37/26 |
| FR | 2 891 163 A1 | 3/2007 | | |

OTHER PUBLICATIONS

Nezhad et al, A New Approach to Mechanochemically Synthesizing Al2O3/Cu—Cr Nanocomposites, 2012, International Journal of Scientific & Engineering Research vol. 3, Issue 4, pp. 1-7.*
Zhang et al, A review on mechanochemical syntheses of functional materials, Jun. 2012, Advanced Powder Technology , 23, pp. 523-531.*
English translation of EP0657408, 1995.*
Marinkovic Z.V. et al., "Microstructural Characterization of Mechanically Activated Zn0-Cr2O3 system" Journal of the European Ceramic Society, May 26, 2005, vol. 25, No. 12, pp. 2081-2084.
Chamberland, B.L. et al., "Synthesis and Properties of Several Members of the Series Cr0(2-x)F(x)" Journal of Solid State Chemistry, Apr. 1973, vol. 6, No. 4, pp. 561-564.
Denis, M.C. et al., "High Energy Ball-Milled Pt and Pt—Ru Catalysts for Polymer Electrolyte Fuel Cells and their Tolerance to CO" Journal of Applied Electrochemistry, 1999, vol. 29, pp. 951-960.
International Search Report (PCT/ISA/210) mailed on Feb. 28, 2014, by the European Patent Office as the International Searching Authority for International Application No. PCT/FR2013/052872.
Qiang, L. et al., "Preparation and Characterization of Iron-based High-temperature Water-gas Shift Catalysts with Ball Milling Method", The Chinese Journal of Process Engineering, vol. 9, No. 3, pp. 613-617, Jun. 30, 2009, (With English Abstract).
Chinese Office Action in corresponding Chinese application No. 201380060833.0, issued on May 24, 2016, 7 pages (with English-language translation, 9 pages.)

* cited by examiner

*Primary Examiner* — Melvin C Mayes
*Assistant Examiner* — Stefanie Cohen
(74) *Attorney, Agent, or Firm* — Buchanan Ingersoll & Rooney P.C.

(57) ABSTRACT

A process for preparing a catalyst, including the reactive milling of a first reagent, which is a chromium oxide compound, with a second reagent, which is a compound of the formula $M_zM'_{1-z}O_xF_y$, M and M' each being an element having an oxidation state greater than or equal to 0, z being from 0 to 1, x being from 0 to 3, y being from 0 to 6, and 2x+y being greater than 0 and less than or equal to 6.

12 Claims, No Drawings

CATALYST PREPARED BY REACTIVE MILLING

FIELD OF THE INVENTION

The invention relates to the preparation of a catalyst, in particular based on chromium oxyfluoride, by reactive milling. The subject of the present invention is also the use of said chromium oxyfluoride as a catalyst, in particular in the fluorination field. A subject of the present invention is also a process for fluorinating a (hydro)halocarbon compound using said chromium oxyfluoride.

TECHNICAL BACKGROUND OF THE INVENTION

Chromium oxides can be used as catalysts in a reaction for exchange or reorganization of halogens in compounds which are hydrocarbon-based or of halogenated hydrocarbons.

The properties of these catalysts can be, inter alia, modulated by the methods for producing them and by the compositions thereof.

Chromium oxide-based catalysts are generally produced by precipitation of salts using alkaline agents, followed by washing, drying and calcining steps. By way of example, mention may be made of document U.S. Pat. No. 6,337,299 describing a process for obtaining a fluorination catalyst comprising a chromium oxide produced by precipitation, followed by steps of drying, compression in the form of granules and calcining.

Chromium oxides can be produced in various crystalline or amorphous forms.

Chromium oxide-based fluorination catalysts may comprise doping agents such as, for example, nickel (FR 2 684 567), vanadium, magnesium or zinc (FR 2 713 633) or indium, gallium, cobalt, nickel, zinc and aluminum (U.S. Pat. No. 6,433,233).

The preparation of catalysts based on doped chromium oxide is generally carried out by coprecipitation. After drying and calcining, the solid is often subjected to a step of treatment with HF gas or with a fluorinated gas, and/or of activation.

The preparation methods as described above are not entirely satisfactory. This is because the coprecipitation method is limited by the solubility range and is consequently not very flexible. It also results in a heterogeneous composition and/or solids with specific surface areas that are not very highly developed, thereby limiting catalytic performance levels. In addition, the abovementioned methods consume large amounts of water and energy.

The applicant has now developed a process for preparing a chromium-based solid which does not have some or any of the drawbacks of the methods described in the prior art.

SUMMARY OF THE INVENTION

The present invention relates to a process for preparing a catalyst, comprising the reactive milling of a first reagent, which is a chromium oxide compound, with a second reagent, which is a compound of formula $M_zM'_{1-z}O_xF_y$, M and M' each being an element having an oxidation state greater than or equal to 0, z being from 0 to 1, x being from 0 to 3, y being from 0 to 6, and 2x+y being greater than 0 and less than or equal to 6.

According to one embodiment, M and M' are elements of columns 1 to 15, preferably from 4 to 15, preferably from 5 to 12, of the Periodic Table of Elements.

According to one embodiment, the catalyst comprises chromium having an oxidation state of between 3 and 5, preferably from 3.1 to 4.5 and more particularly preferably from 3.2 to 4.2.

According to one embodiment, the first reagent is chosen from $CrO_3$, $Cr_2O_3$, $CrO_2$ and combinations thereof.

According to one embodiment, the process comprises, at the end of the reactive milling step, a step of fluorination by bringing into contact with a fluorinating agent, preferably anhydrous hydrofluoric acid.

According to one embodiment, the elements M and M' are chosen from chromium, nickel, magnesium, cobalt, zinc, aluminum, antimony, barium, bismuth, cadmium, calcium, cerium, copper, tin, europium, iron, gallium, germanium, indium, lanthanum, manganese, molybdenum, nickel, niobium, phosphorus, lead, praseodymium, scandium, strontium, tantalum, terbium, thorium, titanium, tungsten, vanadium, yttrium and zirconium; and preferably from chromium, nickel, magnesium, cobalt, zinc, aluminum, antimony, barium, bismuth, calcium, cerium, copper, tin, iron, lanthanum, manganese, molybdenum, nickel, niobium, phosphorus, lead, strontium, tantalum, titanium, terbium, tungsten, vanadium, yttrium and zirconium.

According to one embodiment, the second reagent is chosen from $CaCr_2O_7$, $CaCrO_4$, $Ca_3Cr_2O_8$, $CaCrO_4$, $CrVO_4$, $Cr_2V_4O_{13}$, $NiCr_2O_4$, $NiCrO_4$, $CuCrO_4$, $CdCrF_5$, $Pb_3Cr_2F_{12}$, $Pb_4CrF_{11}$, $Pb_5CrO_8$, $Pb_2CrO_5$, $PbCrO_4$, $Pb_5CrF_{17}$, $Pb_5W_3O_9F_{10}$, $CrF_2$, $CrF_3$, $CrOF_2$, $CuF_2$, $PbF_2$, $BiF_3$, $BiF_5$, $CdF_2$, $NiF_2$, $YF_3$, $MoF_3$, $MoF_4$, $MoF_5$, $MoF_6$, $MoOF_4$, $GeF_2$, $GeF_4$, $SbF_3$, $SbF_5$, $BaF_2$, $LaF_3$, $LaOF$, $PF_3$, $SrF_2$, $WF_4$, $WF_5$, $WF_6$, $WOF_4$, $ZnF_2$, $MnF_3$, $MnF_2$, $SnF_2$, $SnF_4$, $CaF_2$, $NbF_3$, $NbF_4$, $NbF_5$, $NbO_2F$, $MgF_2$, $CeF_4$, $TiF_3$, $TiF_4$, $TaF_5$, $ThF_4$, $FeF_3$, $AlF_3$, $ScF_3$, $CeF_4$, chromium-substituted $Mn_2O_3$, manganese-substituted $Cr_2O_3$, $NiCr_aO_4$ where a is from 1 to 2, $MoO_{2.4}F_{0.6}$, $Mo_4O_{11.2}F_{0.8}$ and combinations thereof.

According to one embodiment, the reactive milling is carried out for a period of from 1 to 96 hours, preferably from 2 hours to 48 hours.

According to one embodiment, the second reagent is provided by a spent catalyst, said spent catalyst preferably comprising chromium, oxygen, fluorine, optionally an additional element and/or coke, or the second reagent is a chromium fluoride, a chromium oxyfluoride or a chromium oxide in which the oxidation state of the chromium is different than that of the first reagent.

A subject of the invention is also a catalyst which can be obtained by means of the process described above.

According to one embodiment, this catalyst is a chromium oxyfluoride, optionally doped with one or two elements M and M'.

A subject of the invention is also the use of the catalyst, in particular in a fluorination reaction.

A subject of the invention is also a process for fluorinating a (hydro)halocarbon compound, comprising the reaction of the (hydro)halocarbon compound with a fluorinating agent, in the presence of a catalyst comprising abovementioned catalyst.

According to one embodiment, the fluorinating agent is anhydrous hydrofluoric acid and/or the (hydro)halocarbon compound is chosen from dichloromethane, perchloroethylene, tetrachloropropene, pentachloroethane, pentachloropropane, pentachlorobutane, trifluoropropene, dichlorotrifluoropropene, chlorotrifluoropropene and combinations thereof.

DETAILED DESCRIPTION OF THE INVENTION

The invention is now described in greater detail and in a nonlimiting manner in the description which follows.

A subject of the present invention is a process for preparing a catalyst (in particular a chromium oxyfluoride), comprising chromium having an oxidation state of between 3 and 5, oxygen, fluorine and, where appropriate, an element M and/or M' (it being possible for M and M' to be in particular metal elements) having an oxidation state greater than or equal to zero, from a first reagent, which is a chromium oxide, and a second reagent, which is a compound $M_zM'_{1-z}O_xF_y$, with M and M' different than one another and being in particular chromium, nickel, magnesium, cobalt, zinc, aluminum, antimony, barium, bismuth, cadmium, calcium, cerium, copper, tin, europium, iron, gallium, germanium, indium, lanthanum, manganese, molybdenum, nickel, niobium, phosphorus, lead, praseodymium, scandium, strontium, tantalum, terbium, thorium, titanium, tungsten, vanadium, yttrium or zirconium; x being a number from 0 to 3, y being a number from 0 to 6, 2x+y being greater than 0 and less than or equal to 6 and z being from 0 to 1; the process optionally also comprising at least one step of fluorination with a fluorinating agent.

Cadmium, gallium, germanium, indium, scandium and thorium are elements which have problems in terms of safety or rarity; thus, it is preferred for the elements M and M' to be chosen from the restricted list comprising chromium, nickel, magnesium, cobalt, zinc, aluminum, antimony, barium, bismuth, calcium, cerium, copper, tin, iron, lanthanum, manganese, molybdenum, nickel, niobium, phosphorus, lead, strontium, tantalum, terbium, titanium, tungsten, vanadium, yttrium and zirconium.

The second reagent can be generated in situ from a precursor (in particular in the form of a salt which does not give a solid residue after calcining, such as carbonate, nitrate, hydroxide, oxyhydroxide or ammonium).

When z is 0 or 1, the second reagent comprises a single element M or M'.

When z is other than 0 and than 1, the second reagent comprises two elements M and M'. According to one embodiment, one of these elements is chromium. According to an alternative embodiment, both these elements are distinct from chromium.

The second reagent comprises in particular two elements, M and M' when the second reagent is provided by a spent catalyst (for example a catalyst based on chromium oxyfluoride doped with nickel, with zinc, etc.). The spent catalyst may be subjected to a pretreatment, for example decoking, or washing in order to eliminate any contaminants, such as Na, Si or Fe.

In the catalyst obtained (which is preferably a chromium oxyfluoride optionally comprising at least one other metal element), the oxidation state of the chromium is greater than 3 and less than 5, advantageously less than or equal to 4.5 and even better still less than or equal to 4.2.

The oxidation state of the chromium in the oxyfluoride that is particularly preferred is greater than or equal to 3.1 or even better still greater than or equal to 3.2.

The second reagent may, for example, be a mixed oxide, fluoride or oxyfluoride chosen from $CaCr_2O_7$, $CaCrO_4$, $Ca_3Cr_2O_8$, $CaCrO_4$, $CrVO_4$, $Cr_2V_4O_{13}$, $MoOF_4$, $NiCr_2O_4$, $NiCrO_4$, $CuCrO_4$, $CdCrF_5$, $Pb_3Cr_2F_{12}$, $Pb_4CrF_{11}$, $Pb_5CrO_8$, $Pb_2CrO_5$, $PbCrO_4$, $Pb_5CrF_{17}$, $WOF_4$ and $Pb_6W_3O_9F_{10}$.

The mixed oxide may also be a solid solution in which Mn is replaced by chromium in $Mn_2O_3$, or the chromium is replaced by Mn in $Cr_2O_3$.

Solid solutions of chromium in NiO of the $NiCr_aO_4$ type, with a between 1 and 2, may also be suitable.

According to one embodiment, the second reagent is a simple fluoride (with x equal to zero), for example chosen from $CrF_2$, $CrF_3$, $CuF_2$, $PbF_2$, $BiF_3$, $BiF_5$, $CdF_2$, $NiF_2$, $YF_3$, $MoF_3$, $MoF_4$, $MoF_6$, $MoF_6$, $GeF_2$, $GeF_4$, $SbF_3$, $SbF_5$, $BaF_2$, $LaF_3$, $PF_3$, $SrF_2$, $WF_4$, $WF_5$, $WF_6$, $ZnF_2$, $MnF_3$, $MnF_2$, $SnF_2$, $SnF_4$, $CaF_2$, $NbF_3$, $NbF_4$, $NbF_5$, $MgF_2$, $CeF_4$, $TiF_3$, $TiF_4$, $TaF_5$, $ThF_4$, $FeF_3$, $AlF_3$, $ScF_3$ and $CeF_4$.

According to one embodiment, the second reagent is a simple oxyfluoride such as $MoO_{2.4}F_{0.6}$, $Mo_4O_{11.2}F_{0.8}$, $NbO_2F$ or $CrOF_2$, or for example a spent catalyst comprising chromium, oxygen and fluorine, optionally an additional element M or M' and coke.

The oxidation state of the chromium in the chromium oxide first reagent may be from 3 to 6. This chromium oxide may in particular be chosen from $CrO_3$, $Cr_2O_3$ and $CrO_2$. It may also be generated in situ from a precursor such as a chromium nitrate, carbonate, hydroxide, ammonium or oxyhydroxide.

The second reagent $M_zM'_{1-z}O_xF_y$ may be a spent catalyst, or else a chromium oxide in which the chromium has an oxidation state different than that of the first reagent. In particular, when the oxidation state of the chromium in the first reagent is equal to 3, at least one among the elements M and M' is an element having an oxidation state greater than 3.

When the second reagent is a chromium oxide, a chromium fluoride or a chromium oxyfluoride, the ratio of the molar amount of the second compound relative to that of the first compound which is used in the reactive milling step depends on the respective state of oxidation of the chromium in the two respective reagents. This molar ratio is denoted R. With the chromium oxide first reagent being denoted $Cr_aO_b$, and given the fact that it is desired for the solid product to be at least 10% and at most 90% fluorinated for example (excessive fluorination rendering it inert), the number $2y/((x+R \cdot b)+2y)$ is preferably from approximately 0.1 to approximately 0.9, in other words the ratio R is preferably approximately from $(1/b) \cdot (0.2y/0.9-x)$ to $(1/b) \cdot (18y-x)$.

When the second reagent does not comprise chromium, the molar ratio R representing the molar amount of the second reagent relative to that of the first reagent (expressed in amount of M and M' relative to the amount of chromium) which is used in the reactive milling step is greater than 0 and preferably less than or equal to 8.5 and advantageously less than or equal to 1.5.

The final chromium oxyfluoride may contain only chromium, oxygen and fluorine, in which case the second reagent is preferably $CrF_3$ or $CrOF_2$ or $CrO_2F_2$ or $CrF_2$. $CrF_3$ and $CrF_2$ can be generated in situ from $(NH_4)_3CrF_6$.

Alternatively, the chromium oxyfluoride may contain a doping agent, in which case the second reagent is advantageously chosen from zinc oxide, nickel oxide, nickel fluoride and manganese oxide.

It is possible to use a combination of different chromium oxides by way of the first reagent, and/or to use a combination of different compounds of formula $M_zM'_{1-z}O_xF_y$ by way of the second reagent.

The present invention implements reactive milling, which comes under mechanochemistry. Mechanochemistry concerns chemical reactions of materials induced directly by the absorption of mechanical energy. Shear, friction and milling methods can involve mechanochemical phenomena. These abrasive phenomena may not only induce an increase in actual surface area through a decrease in the size of the particles, but can also form new alloys via mechanochemistry.

According to Denis et al. (*J. Appl. Electrochem.*, Volume 29, No. 8, 1999, p. 951-960), alloys can be produced by diffusion of the elements in the solid state, promoted by the deviation of the crystalline structure after mechanical strain. In the case of milling, the temperature may increase by some tens of degrees without locally exceeding 300° C.

In the aforementioned and in what follows, the term "reactive milling" is intended to mean a mechanical process of reduction in size of the particles of solid simultaneously inducing a chemical reaction and a modification of the composition of the particles of solid, accompanied by an agglomeration of the particles.

Preferably, the reactive milling is carried out using an energy of from 1 to 10,000 Wh/kg, more particularly preferably from 10 to 1000 Wh/kg.

The energy used during the milling depends on the milling equipment and on the duration of the milling. Thus, in order to bring a solid to micrometric dimensions, an energy of 50 Wh/kg is typically used. A ball mill would require a duration of 1 hour at 50 W/kg.

The reactive milling step can be carried out in a wide range of milling and crushing equipment. Mention may in particular be made of mills containing mobile elements such as balls, cylinders or bars or even containing only particles to be milled which mill themselves autonomously through collisions. The milling may be carried out by any means known to those skilled in the art, for example by centrifugal force or by oscillation or else by a combination of the two.

The reactive milling step may be carried out continuously, semicontinuously or batchwise. The milling may be carried out either dry, or in suspension when the second reagent is a liquid.

Thus, the reactive milling differs from the method used by Chamberland et al., in *Journal of solid state chemistry* 6, 561-564 (1973), in that, in this article, mixtures of $CrO_2$ and $CrF_2$ are milled in a mortar and then placed in a capsule so as to be subjected to a pressure of 60-65 kbar and 1200° C. for 2 hours, so that the reaction between the two species is not carried out by the milling, but by the subsequent heating step.

The advantages of the process according to the present invention are the following:
flexibility: the composition of the solid can be easily modulated with the same production facility;
economy: the process is easily industrializable;
safety: there is no waste nor aqueous discharge;
recyclability: the process allows the recycling of the spent solids (catalysts) provided that they are not excessively polluted with metals;
possibility of obtaining aggregates of micrometric or even millimetric size from the nanometric particles.

The reactive milling differs from simple milling in terms of a structural and textural modification of the solid(s).

The reactive milling parameters are preferably adjusted such that the milled particles agglomerate until a particle distribution having a Dv50 of between 20 and 100 μm, and more particularly between 40 and 80 μm, is obtained. Such a size distribution makes it possible to obtain a powdered solid product which can be easily handled and fluidized.

The process according to the invention may comprise a fluorination step, following the reactive milling step. In particular, when y is equal to zero, the process according to the present invention preferably comprises at least one fluorination step.

Preferably, the fluorinating agent is anhydrous hydrofluoric acid.

The fluorination step according to the process of the present invention may be carried out at a temperature of between 100 and 450° C., preferably between 200 and 350° C., for a period of between 1 and 50 hours.

A subject of the present invention is also the use of the chromium oxyfluoride prepared according to the process described above, as a catalyst. Preferably, this chromium oxyfluoride is used as a catalyst in a fluorination reaction.

Finally, a subject of the present invention is a process for fluorinating a (hydro)halocarbon compound. The fluorinating agent is preferably anhydrous hydrofluoric acid.

The (hydro)halocarbon compound can in particular be chosen from dichloromethane, perchloroethylene, tetrachloropropene, pentachloroethane, pentachloropropane, pentachlorobutane, trifluoropropene, dichlorotrifluoropropene and chlorotrifluoropropene.

EXPERIMENTAL SECTION

A Retsch planetary mill, model PM400MA, with a grinding jar/sun wheel rotational speed ratio of 1/-3, is used. Grinding jars of 125 ml are used. The milling is carried out in the air, for periods of 60 minutes, with a sun wheel rotational speed of 400 rpm. Zirconium oxide balls 10 mm in diameter, that is to say 30 balls, are used. The sample volume is from 15 to 50 ml.

Use is made of chromium oxide $Cr_2O_3$ from Sigma-Aldrich, having a particle size of approximately 50 microns (catalog ref. 393703-500G) and a molar mass of 151.99 g/mol; chromium oxide $CrO_3$ from Sigma-Aldrich (catalog ref. 236470-500G) having a molar mass of 99.99 g/mol and a specific surface area of 5 $m^2/g$; and chromium nitrate nonahydrate $(Cr(NO_3)_3.9H_2O)$ from Sigma-Aldrich (catalog reference 239259-500G) having a molar mass of 400.15 g/mol.

Use is also made of nickel oxide (NiO) from Sigma-Aldrich (catalog ref. 399523) of less than 50 microns, and having a molar mass of 74.69 g/mol; of terbium oxide $(Tb_4O_7)$ (catalog ref. 253952-10G) having a molar mass of 747.7 g/mol; and zinc oxide (ZnO) (catalogue reference 205532-100g) having a molar mass of 81.39 g/mol.

Use is made of chromium fluoride freshly prepared as follows: an aqueous solution of chromium nitrate is prepared by mixing 400 g of chromium nitrate (1 mol) in 7 liters of demineralized water, and approximately 1 kg of a 10% by weight aqueous ammonia solution is then added in order to bring about the precipitation of a chromium hydroxide. The precipitate is filtered off and washed with water, until the washing water has a stable pH. The precipitate is dried under air at 120° C. in an oven, overnight, and crushed and milled so as to obtain a powder of less than 50 microns. The resulting powder is mixed with 2% by weight of graphite in order to allow pelleting in the form of cylinders 5 mm in diameter and 5 mm in height, with a central hole having an internal diameter of 2.5 mm. The pellets are loaded into a hastelloy tube having an internal diameter of 21 mm, and then calcined at 400° C., for 2 hours under a nitrogen stream.

The pellets are then treated with a stream of hydrogen fluoride in a mixture with nitrogen, up to a temperature of 360° C.

The solid obtained is characterized by a specific surface area of 41 m$^2$/g and it is amorphous to X-rays.

Example 1

76 g of $Cr_2O_3$, 4 g of ZnO and 18 g of NiO are mixed. The mixture has a specific surface area before milling of 4.5 m$^2$/g.

After reactive milling for one hour under the conditions described above, the mixture has a (BET) specific surface area of 8.3 m$^2$/g.

Example 2

54 g of chromium fluoride and 25 g of $CrO_3$ are mixed. The mixture has a specific surface area before milling of 15.2 m$^2$/g.

After reactive milling for one hour under the conditions described above, the mixture has a (BET) specific surface area of 26 m$^2$/g.

Example 3

76 g of $Cr_2O_3$, 15 of NiO and 5 g of $Tb_4O_7$ are mixed. The mixture has a specific surface area before milling of 4.7 m$^2$/g.

After reactive milling for one hour under the conditions described above, the mixture has a (BET) specific surface area of 7.6 m$^2$/g.

Example 4

100 g of the chromium hydroxide obtained during the preparation of the chromium fluoride, and 50 g of $CrO_3$ are mixed.

The efficiency of the reactive milling is also monitored by XRD analysis (source Cu, Kα) of the mixtures. Each mixture is analyzed before and after milling, and the efficiency of the milling is characterized by the disappearance and the widening of the X-ray diffraction lines. The products obtained are characterized by broad peaks reflecting the more amorphous nature of the solids formed.

In example 1, the X-ray diffraction line at 33.6° (characteristic of $Cr_2O_3$) has a relative intensity of 20% of that of the starting mixture. The X-ray diffraction line at 43.3° (characteristic of NiO) has a relative intensity of 5% of that of the starting mixture.

In example 2, the modification of the starting mixture during the reactive milling is illustrated by the appearance of a line at 28.5°.

In example 3, the X-ray diffraction line at 33.6° has a relative intensity of 27% of that of the starting mixture.

In example 4, a wide diffraction line at approximately 28.5° is observed.

The invention claimed is:

1. A process for preparing a catalyst, comprising the reactive milling of a first reagent, which is a chromium oxide compound, with a second reagent,
wherein the second reagent is selected from the group consisting: of $CaCr_2O_7$, $CaCrO_4$, $Ca_3Cr_2O_8$, $Cr_2V_4O_{13}$, $NiCr_2O_4$, $NiCrO_4$, $CdCrF_5$, $Pb_3Cr_2F_{12}$, $Pb_4CrF_{11}$, $Pb_5CrO_8$, $Pb_2CrO_5$, $PbCrO_4$, $Pb_5CrF_{17}$, $Pb_5W_3O_9F_{10}$, $CrF_2$, $CrF_3$, $CrOF_2$, $PbF_2$, $BiF_3$, $BiF_5$, $CdF_2$, $NiF_2$, $YF_3$, $MoF_3$, $MoF_4$, $MoF_5$, $MoF_6$, $MoOF_4$, $GeF_2$, $GeF_4$, $SbF_3$, $SbF_5$, $BaF_2$, $LaF_3$, $LaOF$, $PF_3$, $SrF_2$, $WF_4$, $WF_5$, $WF_6$, $WOF_4$, $ZnF_2$, $MnF_3$, $MnF_2$, $SnF_2$, $SnF_4$, $CaF_2$, $NbF_3$, $NbF_4$, $NbF_5$, $NbO_2F$, $MgF_2$, $CeF_4$, $TiF_3$, $TiF_4$, $TaF_5$, $ThF_4$, $FeF_3$, $AlF_3$, $ScF_3$, chromium-substituted $Mn_2O_3$, manganese-substituted $Cr_2O_3$, $NiCr_aO_4$ where a is from 1 to 2, $MoO_{2.4}F_{0.6}$, $Mo_4O_{11.2}F_{0.8}$ and combinations thereof.

2. The process as claimed in claim 1, wherein the catalyst comprises chromium having an oxidation state of between 3 and 5.

3. The process as claimed in claim 1, wherein the first reagent is selected from the group consisting of $CrO_3$, $Cr_2O_3$, $CrO_2$ and combinations thereof.

4. The process as claimed in claim 1, comprising, at the end of the reactive milling step, a step of fluorination by bringing into contact with a fluorinating agent.

5. The process as claimed in claim 1, wherein the reactive milling is carried out for a period of from 1 to 96 hours.

6. The process as claimed in claim 1, wherein the second reagent is provided by a spent catalyst, or wherein the second reagent is selected from the group consisting of chromium fluorides, chromium oxyfluorides or chromium oxides in which the oxidation state of the chromium is other than that of the first reagent.

7. The process as claimed in claim 1, wherein the reactive milling produces milled agglomerated particles having a $Dv_{50}$ of between about 20 and about 100 μm.

8. The process as claimed in claim 1, wherein the reactive milling produces milled agglomerated particles having a $Dv_{50}$ of between about 40 and about 80 μm.

9. A catalyst which can be obtained by the process as claimed in claim 1.

10. The catalyst as claimed in claim 9, which is a chromium oxyfluoride, optionally doped with one or two elements M and M'.

11. A process for fluorinating a (hydro)halocarbon compound, comprising the reaction of the (hydro)halocarbon compound with a fluorinating agent, in the presence of a catalyst comprising the catalyst as claimed in claim 9.

12. The fluorinating process as claimed in claim 11, wherein the fluorinating agent is anhydrous hydrofluoric acid and/or wherein the (hydro)halocarbon compound is selected from the group consisting of dichloromethane, perchloroethylene, tetrachloropropene, pentachloroethane, pentachloropropane, pentachlorobutane, trifluoropropene, dichlorotrifluoropropene, chlorotrifluoropropene and combinations thereof.

* * * * *